(12) United States Patent
Heneveld

(10) Patent No.: US 10,512,454 B2
(45) Date of Patent: Dec. 24, 2019

(54) NEEDLE AND SNARE GUIDE APPARATUS FOR PASSING SUTURE

(71) Applicant: SUTURE EASE, INC., San Jose, CA (US)

(72) Inventor: Scott Heneveld, Whitmore, CA (US)

(73) Assignee: SUTURE EASE, INC., San Jose, CA (US)

( * ) Notice: Subject to any disclaimer, the term of this patent is extended or adjusted under 35 U.S.C. 154(b) by 31 days.

(21) Appl. No.: 15/096,610

(22) Filed: Apr. 12, 2016

(65) Prior Publication Data

US 2016/0220238 A1 Aug. 4, 2016

Related U.S. Application Data

(63) Continuation of application No. 13/787,243, filed on Mar. 6, 2013, now Pat. No. 9,393,011.

(Continued)

(51) Int. Cl.
*A61B 17/00* (2006.01)
*A61B 17/04* (2006.01)
*A61B 17/06* (2006.01)

(52) U.S. Cl.
CPC ...... *A61B 17/0057* (2013.01); *A61B 17/0469* (2013.01); *A61B 17/0482* (2013.01); *A61B 17/0483* (2013.01); *A61B 17/0493* (2013.01); *A61B 2017/00637* (2013.01); *A61B 2017/00663* (2013.01); *A61B 2017/0472* (2013.01); *A61B 2017/0496* (2013.01);
(Continued)

(58) Field of Classification Search
CPC ............ A61B 17/0482; A61B 17/0469; A61B 17/0483; A61B 2017/06009; A61B 2017/06042; A61B 2017/0496; A61B 2017/0472; A61B 17/0485

See application file for complete search history.

(56) References Cited

U.S. PATENT DOCUMENTS 5,954,732 A * 9/1999 Hart .................. A61B 17/0469
606/144
7,824,419 B2 11/2010 Boraiah
(Continued)

OTHER PUBLICATIONS

Office Action dated Oct. 11, 2016 from related U.S. Appl. No. 14/800,532, 17 pages.
(Continued)

*Primary Examiner* — Anh T Dang
(74) *Attorney, Agent, or Firm* — Innovation Capital Law Group, LLP; Vic Lin

(57) ABSTRACT

A trocar wound closure system includes a suture passing needle and a guide for directing the needle through the wound site. A distal portion of the needle includes a capture rod with a slot. An obturator tube with a cutout section can be axially actuated to align the cutout section with the slot, and then moved out of alignment so as to capture the suture. The guide includes at least two tracks for directing the needle through the tissue track. A snare loop is located adjacent to the exit of each track, and configured to be actuated from a radially extended configuration to a retracted configuration so as to capture the suture section inserted through each loop. Radially expandable arms at distal section are movable between an expanded configuration and a slender configuration.

27 Claims, 17 Drawing Sheets

Related U.S. Application Data

(60) Provisional application No. 61/723,262, filed on Nov. 6, 2012, provisional application No. 61/610,354, filed on Mar. 13, 2012.

(52) U.S. Cl.
CPC .............. *A61B 2017/06009* (2013.01); *A61B 2017/06014* (2013.01); *A61B 2017/06042* (2013.01)

(56) References Cited

U.S. PATENT DOCUMENTS

| | | |
|---|---|---|
| 8,109,943 B2 | 2/2012 | Boraiah et al. |
| 9,668,727 B2 | 6/2017 | Heneveld |
| 2002/0107526 A1 | 8/2002 | Greenberg et al. |
| 2004/0068273 A1 | 4/2004 | Fariss et al. |
| 2010/0262166 A1 | 10/2010 | Boraiah et al. |
| 2011/0112557 A1 | 5/2011 | Beeley |
| 2011/0245850 A1* | 10/2011 | van der Burg ..... A61B 17/0401 606/145 |
| 2012/0191133 A1 | 7/2012 | Ferree |
| 2013/0310856 A1 | 11/2013 | Sherts et al. |

OTHER PUBLICATIONS

Notice of Allowance dated Mar. 16, 2017 from corresponding U.S. Appl. No. 14/800,532, 18 pages.
Notice of Allowance dated Jun. 16, 2016 from related U.S. Appl. No. 13/787,243, 17 pages.
Communication pursuant to Article 94(3) EPC dated Sep. 22, 2017 from corresponding European Application No. 13761889.8.

* cited by examiner

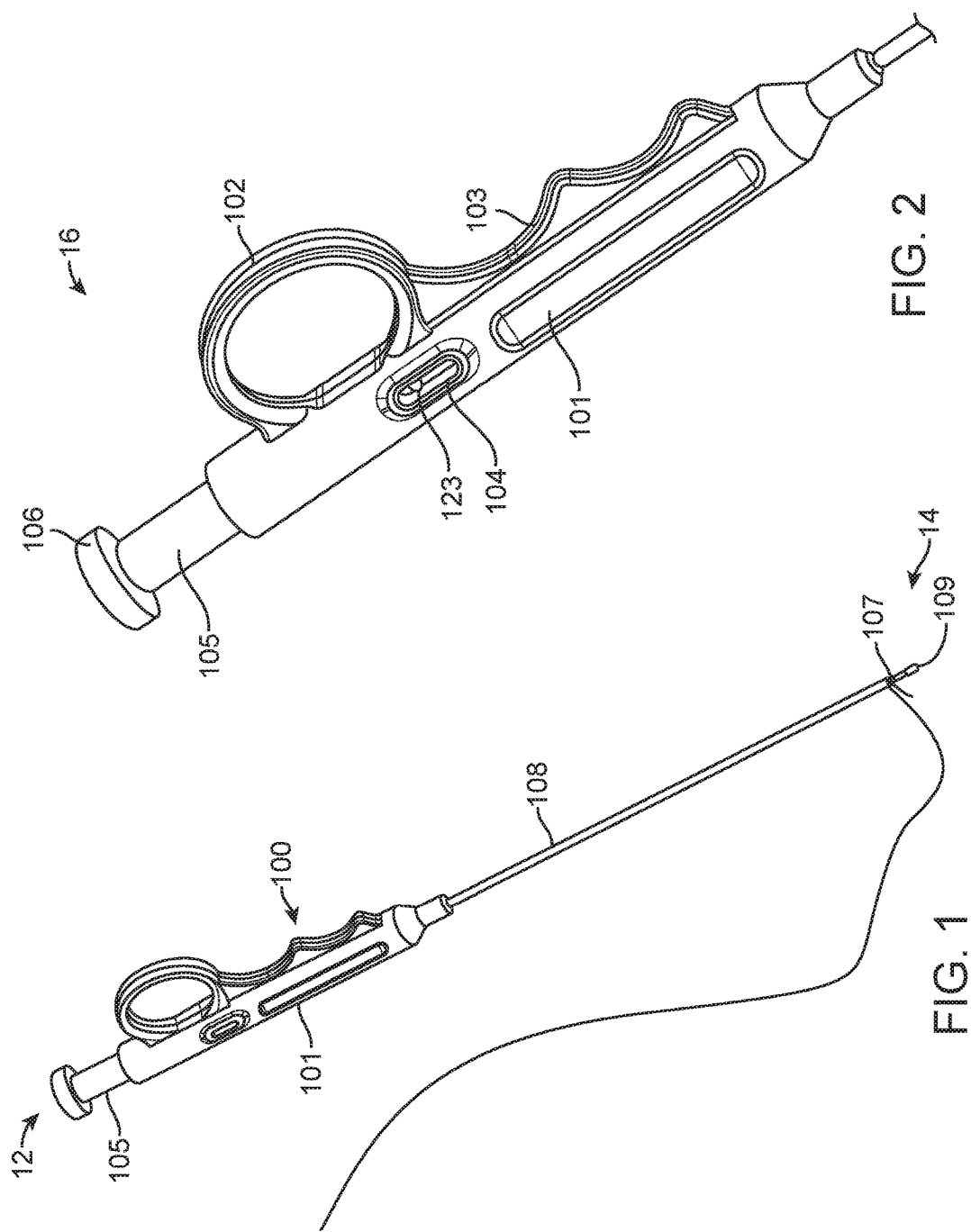

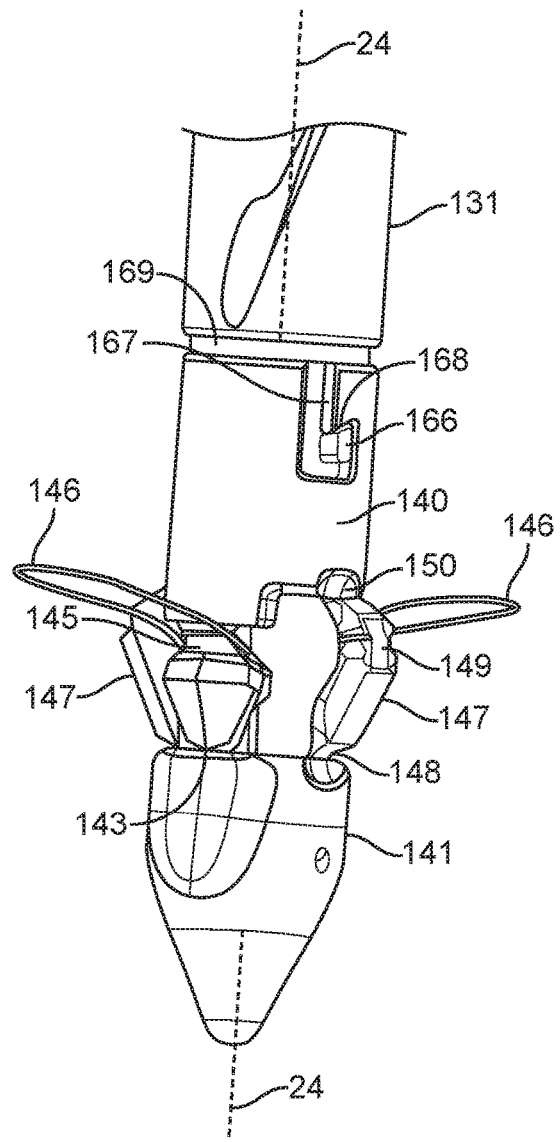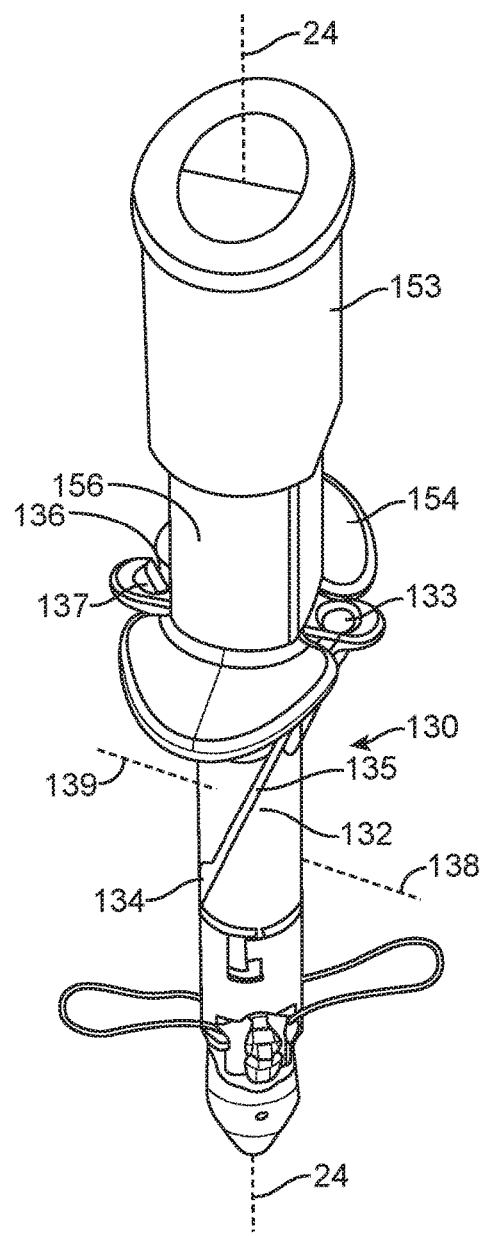

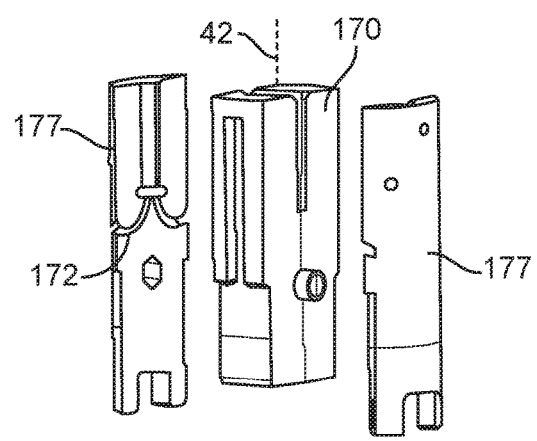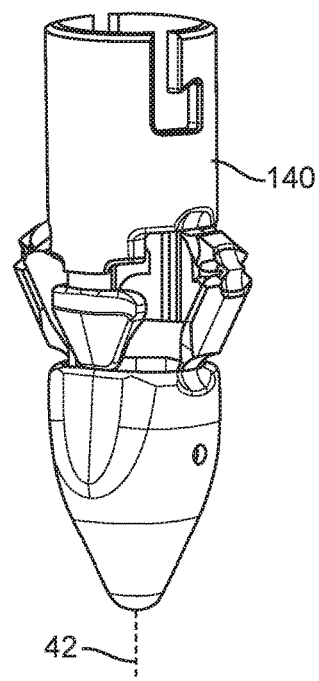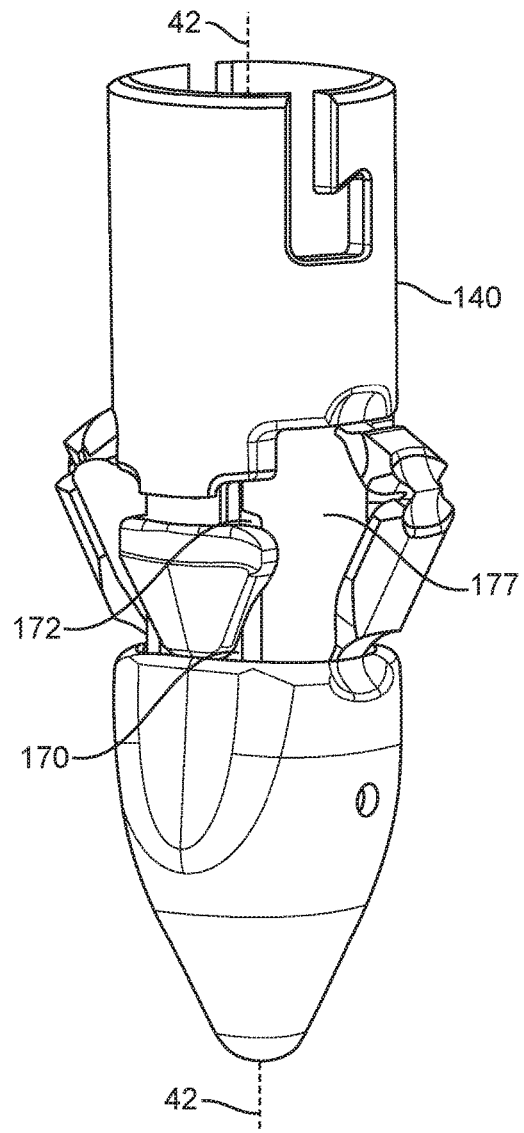
FIG. 10A
FIG. 10B

NEEDLE AND SNARE GUIDE APPARATUS FOR PASSING SUTURE

RELATED APPLICATIONS

This application is a continuation of U.S. application Ser. No. 13/787,243. This application relates to, claims priority from, and incorporates herein by reference, as if fully set forth, U.S. Provisional Patent Application Ser. No. 61/610,354 filed on Mar. 13, 2012 and entitled "METHOD AND SNARE GUIDE APPARATUS FOR PASSING SUTURE."; U.S. Provisional Patent Application Ser. No. 61/723,262 filed on Nov. 6, 2012 and entitled "METHOD AND SAFETY NEEDLE APPARATUS FOR PASSING SUTURE."

BACKGROUND OF THE INVENTION

Field of the Invention

This invention relates to surgical instruments for approximation, ligation and fixation of tissue using a suture, and particularly to the approximation of tissue separated by mean of an endosurgical trocar being inserted into a body cavity.

Description of Prior Art and Related Information

Numerous methods currently exist for performing laparoscopic procedures. One of the more commonly used methods is known as closed laparoscopy which utilizes a sharp needle (e.g., Veress needle) to puncture the abdominal wall and insufflate the abdominal cavity with an inert gas such as carbon dioxide through the needle. This process of insufflating the cavity separates the abdominal wall from the underlying organs creating a gap for the surgeon to work within. A trocar/cannula system is then used to maintain the insufflated cavity and provide a working portal for which instruments can be passed into and out of the abdominal cavity to perform various surgical procedures. When the procedure is completed, it is desirable for the surgeon to close the incision site using suture material to minimize the risk of adverse post-operative events.

One of the post-operative complications associated with this procedure is the incidence of trocar site hernias, where a portion of an organ or fatty tissue protrudes out through the hole in the abdominal wall created by the trocar access portal. It is believed that improper closure, or complete lack of closure, of the incision site at the peritoneum is the primary cause of these hernias which form during the post-operative period ranging from several days to several months following the procedure. Traditional methods of wound site close require an additional set of instruments (suture passers, guides, etc.) to be introduced into the surgery. A number of these instruments have been previously disclosed. However, the prior art related to trocar wound site closure instrumentation are typically cumbersome to use and do not provide for a simple, reproducible, and reliable means of closing the wound site.

BRIEF SUMMARY OF THE INVENTION

A preferred system according to the invention comprises a surgical instrument as well as a surgical instrument set that may have certain functions. First, the system may have the capabilities to provide entry into the abdominal cavity and subsequently insufflating the cavity for use in laparoscopic surgical procedures. In the preferred embodiment, the system comprises a needle apparatus having a sharp needle tip and an insufflation channel to facilitate penetration into the abdominal cavity and insufflation. A unique obturator tip is provided to shield the sharp needle tip upon insertion into the cavity. Second, the system may have the capabilities to close the fascial/peritoneal layer at the trocar wound site in a quick, consistent and reproducible manner at the end of the procedure. To facilitate closure of the wound, the system includes the same needle used in combination with a guide apparatus which has suture capture features disposed at or near the distal tip.

The needle apparatus may also serve as a suture passer, in that it has the ability to carry and retrieve suture through tissue layers for suturing closed the wound site. The needle apparatus also has the ability to insufflate the abdomen during the laparoscopic procedure. The needle apparatus may comprise several components including: a handle, actuation mechanism, a connector for connecting the needle to a gas line, a capture rod, an outer needle shaft, and a spring loaded safety tip on a hollow obturator tube.

In a preferred embodiment, a handle at the proximal end of the needle apparatus allows for single-handed or double-handed use. The handle may also contain a finger loop or loops for additional security while holding the needle. An actuator mechanism may be disposed adjacent to the handle and configured for the deployment and retraction of the capture rod used to secure the suture material within the tip of the needle. The preferred actuator mechanism may include a sliding plunger that translates along the long axis of the handle that moves the capture rod between a first position in an axially extended configuration and a second position in an axially retracted configuration. The actuator may be spring loaded in one direction such that the capture rod is biased to the retracted position. This may allow the suture to be passively captured without actuation of the plunger. The handle and actuator means may be constructed from metals (such as stainless steel, titanium or aluminum) or plastics (such as polyacetal, nylon, polypropylene, polyether-ether-ketone, or polycarbonate), or any combination of the two.

A long outer needle shaft may be connected to the proximal handle and extends distally over a length that may range from 2-38 centimeters, or more preferably between 10-20 centimeters. The outer needle shaft may have a sharp tip, or needle peak, at the distal-most point to ease the insertion of the needle through the various tissue layers. The outer shaft may house an obturator tube that has a hollow, unobstructed inner lumen, with a blunt tip. The obturator tube may also house a capture rod used for securing the suture for passing through tissue. The outer needle shaft, obturator tube and capture rod would optimally be constructed from metals such as stainless steel, titanium or aluminum.

The distal-most end of the obturator tube may have a blunt or rounded plug or surface at the tip. The entire obturator tube may be spring loaded to allow for the blunt tip to translate away from the tip of the needle when it is loaded, and passively travel back to the tip of the needle when it is unloaded. The obturator spring may be housed within the handle. The spring loaded obturator would serve as a safety mechanism for protecting the internal organs within the abdomen after the needle is passed through the abdominal wall.

A portion of the wall of the outer needle shaft may be cutout near the distal tip which may be used to create a slot to accommodate the suture during the suture passing process. Similarly, a portion of the wall of the obturator tube may be cut out near the distal tip of the tube to provide an opening for the capture rod to secure the suture to the wall of the outer needle shaft. The window cutout in the obturator tube must be long enough such that it can accommodate the suture as it travels back and forth. Lastly, the capture rod has a slot with one or more ramped faces. A distal ramped surface on the capture rod slot is used to capture the suture against the outer needle shaft. A proximal ramped surface may assist in pushing the suture out of the window in the obturator tube, facilitating the release of the suture from the needle.

The needle capture rod is used to secure the suture to the needle for suture passing activities. Initially the actuator may be pressed to extend the capture rod and expose the slot in the capture rod. A section of suture may be placed into the slot, and the actuator is released to retract the capture rod. As the capture rod retracts, the suture becomes trapped between the distal surface of the slot in the capture rod and the cutout in the outer needle shaft. When the suture needs to be released, the actuator may be pressed again to extend the capture rod. As the capture rod is extended the proximal face of the slot may push the suture material out of the cutout in the obturator tube and away from the needle shaft.

In another preferred embodiment, a luer connector or other quick connect type device may be disposed on the proximal handle to provide an entry passageway for the gas to enter into the needle. The unobstructed inner lumen of the obturator tube may allow for the passage of an inert gas for insufflation of the abdomen.

The guide apparatus may serve dual purposes, as it first may be used to guide the needle through the abdominal wall in a repeatable manner, and second used to capture the suture material after it is passed into the abdominal wall. The guide may comprise a slotted barrel, collapsible barrel tip, plunger, main shaft, cap, suture capturing snare cord, and guide tubes along with various fasteners and springs.

The slotted barrel may have two slotted channels to accommodate the passage of the needle. The entries and exits of the two channels may be spaced 180 degrees radially apart from each other such that the stitch can be placed on opposing sides of the wound. The channels' purpose is to guide the needle repeatedly through the same tissue thickness and into the suture snare cord, where the suture can be released. The trajectory of the channels is referenced off the inner wall of the peritoneum such that approximately 5-15 millimeters of tissue bite is achieved from the periphery of the wound. The proximal ends of the channels may have a widened and or tapered opening to ease the entry of the needle into the channels. Slots in the channels will allow for the middle section of the length of suture to be released from the constraints of the guide channels. The width of the slots in the channels should be large enough for the suture to easily be released from the channels, yet small enough to not allow the needle to exit the channel or get caught against it.

The guide may comprise a main shaft that is slidably disposed within the slotted barrel of the guide. The main shaft may be used to actuate the expanding arms, comprising living hinges in the preferred embodiment on the collapsible barrel tip. One or more expanding arms may be used to locate the guide against the inner peritoneal wall as a reference point to ensure consistent tissue bite depth of the needle, as previously described. The main shaft may be spring loaded in a proximal position such that the expanding arms are biased to a radially expanded position where the outer profile of the arms exceeds the diameter of the slotted barrel. As the main shaft moves distally, the arms may be contracted such that aligns their outer diameter with the outer diameter of the slotted barrel in a continuous slender fashion. The main shaft may be connected at the distal end to the barrel tip, and connected to the plunger on the proximal end.

The distal end of the barrel tip may have a blunt tip to minimize the potential of harm or damage to the adjacent tissues during insertion. Moving proximally away from the blunt tip, the outer wall of the barrel tip may have a tapered region that gradually radially increases to the outer profile of the guide as designated by the outer diameter of the slotted barrel. The tapered section may facilitate the ease of insertion of the guide into the trocar wound site.

The barrel tip may have one or more stop tabs that provide a hard stop for the barrel tip as the expanding arms are actuated, to prevent excessive flexion in the hinge material. Along the length of the stop tabs, a cutout section may exist for the snare loop to be retracted into for capturing the suture material against the guide.

The guide may have a slider that is used to actuate the snare cord material. The slider may be slidably disposed on the slotted barrel. Two snare cords may be connected at their ends to the slider body, with a loop formed at the distal tip of the guide. The slider may be spring loaded such that the snare cords are biased into a radially extended position. As the slider is pulled proximally, the snare cord is retracted against the extension arms of the barrel tip. As the slider is released distally, the snare cord is radially extended out and away from the barrel to create two snare loops for the suture to be passed into. The slider may have two tabs that can be used to pull the slider proximally using one or more fingers on each tab. The snare cords may be constructed from a mono- or multi-filament wire that has the flexibility to easily bend and conform to various geometries yet stiff enough to create a self-supported snare loop that extends generally perpendicular to the long axis of the guide. Materials that may be used to construct the snare cord include plastics such as nylon, polyethylene, polyester or polypropylene or metals such as stainless steel or nitinol.

A plunger at the proximal end of the guide may be used to provide a counterforce when pulling on the slider. As the plunger is pushed and the slider is simultaneously pulled, the snares will move into the retracted position first, and then the expanding arms are retracted into the slender configuration. As the slider is released, the spring forces will extend the snares to the extended position and the expanding arms will be converted to the radially expanded condition.

In another embodiment, the snares may include a basket element to prevent the needle from traversing deeply into the abdominal cavity and causing potential harm.

The basic procedural steps of the utilization of the suturing system may flow as follows. At the end of the surgical procedure, the trocar is removed from the body exposing the wound. The slider on the guide is pulled up against the plunger to contract the flexing arms and retract the snares such that the profile of the guide is at its minimum. The guide can then be inserted into the wound with the plunger continually pulled against the slider. The slider and plunger are then released expanding the arms and deploying the snares. The guide can be pulled upward and away from the body cavity until the arms rest against the inner wall of the peritoneum. A short tail at one end of the suture is secured by the capture rod in the tip of the needle. The needle, with suture, is then passed through a first needle channel in the guide and is advanced through the guide, tissue and snare, into the abdominal cavity. The needle then releases the suture into the cavity, and is retracted from the body. A second short tail at the second free end of the suture is then secured by the capture rod in the needle. The needle, with suture, is then passed through the second needle channel in the guide and advanced through the guide, tissue and snare, into the abdominal cavity. The needle then releases the suture into the abdominal cavity and removed from the guide and body. The remaining loop of suture outside the body may then be released from each of the slots in the needle tracks. The slider on the guide is then again pulled against the plunger to retract the snares, capturing the free ends of suture, and contract the flexing arms allowing the guide to be removed from the wound, carrying the suture with it. Once outside the body, the snares may need to be deployed enough to release the free ends of the suture. Lastly, a knot may be tied and pushed down into the wound to close the trocar puncture site.

In an alternative procedure, the guide may be used to place a FIG. 8 stitch using two separate sutures rather than a single stitch using only one suture. The guide is initially inserted into the wound as previously described. A short tail at a first end of a first suture is loaded into the needle, passed through the first channel of the guide, and released into the abdominal cavity. At this point a short tail at the second end of the first suture is loaded into the needle, and passed through the second channel. The guide may then be rotated approximately 90 degrees from the initial orientation of the first suture passing. A short tail at one end of a second suture may be loaded into the needle, passed through the first channel of the guide, and released into the abdominal cavity. The needle is retracted and then a tail from the opposing end of the second suture is loaded and passed through the second channel of the guide and released into the abdominal cavity. The slider is pulled and the guide is removed from the wound with all four ends of suture captured in the snares. Knots may then be tied in each of the individual sutures to close the wound.

The basic procedural steps for abdominal entry and insufflation of the cavity may flow as follows. The needle is used to enter the abdominal cavity using standard closed laparoscopic techniques. A gas line is connected to the handle allow for an inert gas to be passed into the abdominal cavity. The inert gas is then turned on until the cavity reaches an appropriate level of insufflation to allow for the procedure to be performed with appropriate visualization. The needle is then removed, and a trocar is inserted into the puncture site to perform the procedure.

BRIEF DESCRIPTION OF THE DRAWINGS

FIG. 1 illustrates an oblique view of a preferred embodiment of a needle.

FIG. 2 illustrates a perspective side view of a proximal end of the needle.

FIG. 7 illustrates an oblique view of the distal tip of the guide with radially expanded arms and snare loops.

FIG. 8 illustrates an oblique view of the guide reveals pathways for suture passing.

FIG. 10A illustrates an exploded view of barrel tip components.

FIG. 10B illustrates an isometric view of barrel tip components.

Figure 3:
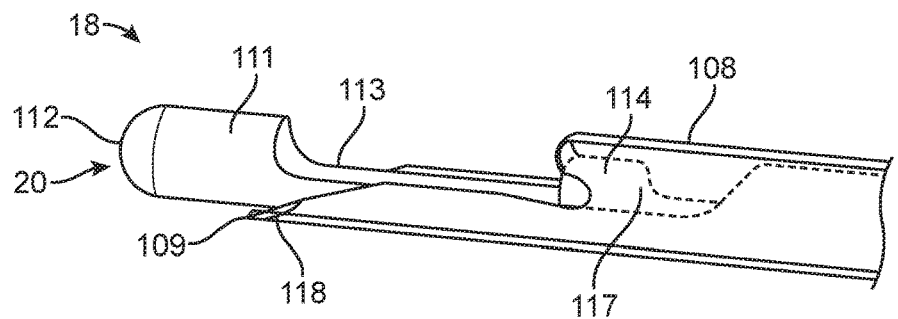
FIG. 3 illustrates a perspective side view of a distal end of the needle.

The various embodiments of the invention can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS

In a preferred embodiment, a system is provided for closing trocar wound sites. The system comprises a suture engagement device and a guide to direct the device through the body tissues.

An improved needle and guide instrument set is further described below as it allows for the surgical placement of suture to be completed "blind," namely, without the aid of an endoscope for direct visualization of the abdominal cavity. This may be advantageous in certain surgical procedures where an endoscope is not being used or does not provide adequate visualization of the surgical site.

A preferred embodiment of a suture engagement device or suture passing needle, or simply needle, 100 is shown in FIG. 1. The needle 100 may simply have a handle 101 and actuator 105 at the proximal end 12. An outer tube 108 is connected to the handle 101 that terminates with a suture capture mechanism 107, sharp needle tip 109, and spring loaded safety tip 112 at the distal end 14 of the needle 100, as shown in FIG. 3.

FIG. 2 illustrates a closer view of the proximal portion 16 of the needle 100. The base of the proximal end 12 of the needle 100 is a main handle or housing 101. The handle 101 may have a finger loop 102 that may accommodate one or more fingers, as well as a series of one or more grooves 103 to accommodate the placement of additional fingers. The finger loop 102 and grooves 103 may provide the user with a comfortable, secure grip of the device and provide greater control when handling the device 100. Slidably disposed within the housing 101 is an actuator 105 that may be used to control a suture capture mechanism 107 at the distal tip of the needle 101. At the proximal end of the actuator 105, an enlarged surface 106 may provide an ergonomic location for a thumb or other finger to trigger the actuator 105. The length travel of the actuator 105 may be constrained by a pin 123 that connects to the actuator 105 and slides within a slot 104 on the handle 101. The pin 123 also serves the purpose of rotationally constraining the actuator 105.

FIG. 3 illustrates a closer view of the distal portion 18 of the needle 100. An obturator tube 111 may be slidably disposed within an outer tube 108, and a capture rod 114 may be slidably disposed within the obturator tube 111. The outer tube 108 terminates at a sharp tip 109 that may have two or more beveled edges 118 to facilitate the ease of passage of the needle 100 through tissue. The obturator tube 111 has a blunt surface 112 at its distal end 20 and may be used to serve as a safety tip for the needle 100. The obturator tube 111 may be spring loaded such that it can passively travel between an axially extended and retracted position. Initially, the obturator tube 111 may be biased in the extended position where the blunt surface 112 extends further distally than the sharp tip 109 of the outer tube 108. As the distal tip of the needle 100 is pushed into the tissue with enough load to overcome the force of the spring, the obturator tube 111 may retract proximally, ultimately exposing the sharp tip 109 of the outer tube 108. The sharp tip 109 and edges 118 may then minimize the trauma to the tissue layers as the needle 100 is inserted. Once the tip 109 of the needle 100 enters the body cavity, the obturator tube 111 may passively return to the distally extended position shielding the sharp tip 109 from inadvertently damaging the tissue structures within the body cavity. The purpose of the capture rod 114 is to secure the suture to the needle 100, in a manner further described below.

Figure 4A:
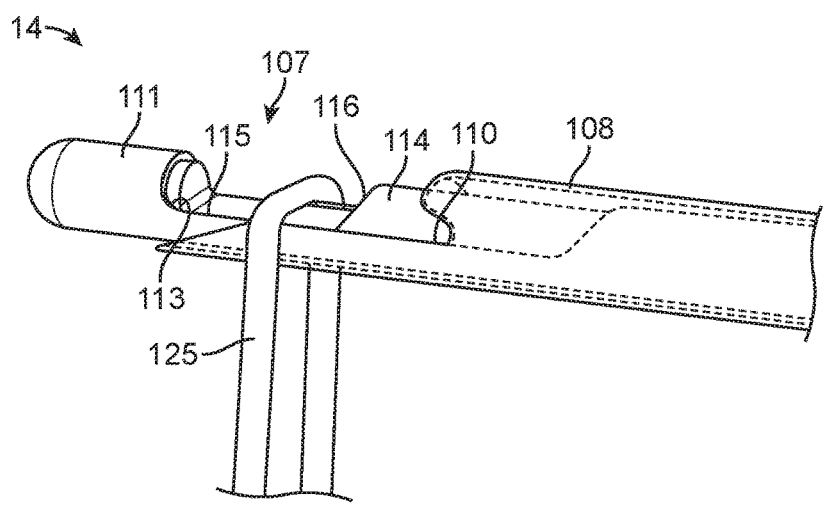
FIG. 4A illustrates a perspective side view of a strand of suture being loaded into the needle with an extended capture rod.
Figure 4B:
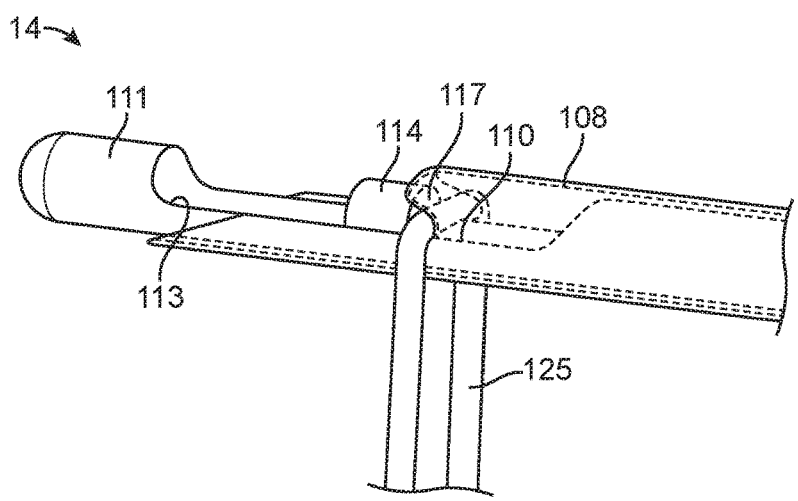
FIG. 4B illustrates a perspective side view of a strand of suture captured by the needle after retraction of the capture rod.

In FIGS. 4A and 4B, the suture capture mechanism 107 at the distal end 14 of the needle 100 preferably comprises a channel 110 in the outer tube 108, a cutout section 113 of the obturator tube 111, and a slot 115 in a capture rod 114. The suture capture mechanism 107 may function through the movement of the capture rod 114 between an axially extended and retracted position that is controlled by the actuator 105 at the proximal end 12 of the needle 100. In FIG. 4A, the capture rod 114 is shown in the extended position such that a strand of suture 125 can be placed through the cutout 113 in the obturator 111 and into the slot 115 of the capture rod 114. In this axially extended position, the obturator cutout 113 is open to, and aligned with, the capture rod slot 115 in order to receive the suture 125. In FIG. 4B, the capture rod 114 is shown in the axially retracted position such that the strand of suture 125 is secured between the channel 110 of the outer tube 108 and the distal face 117 of the slot 155 in the capture rod 114. When the suture 125 needs to be released, the actuator 105 returns the capture rod 114 to the extended position. A proximal face 116 of the capture rod 114, shown in FIG. 4A, may aid in pushing the suture 125 out of the obturator cutout 113 and away from the outer profile of the outer tube 108.

Figure 5A:
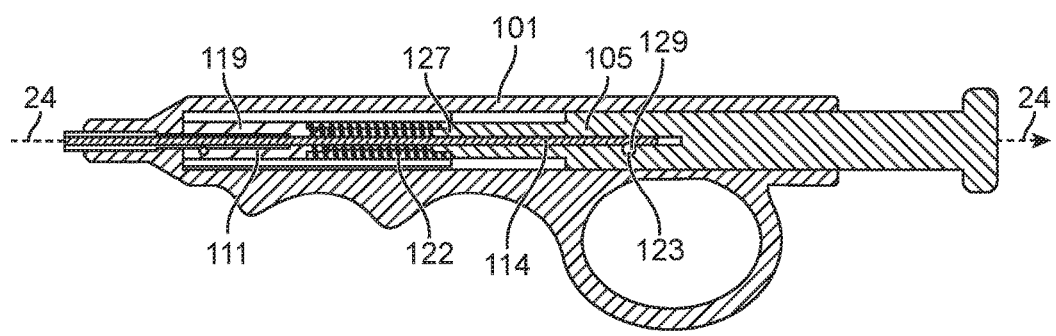
FIG. 5A illustrates a cross-sectional view of the needle demonstrating the internal components.
Figure 5B:
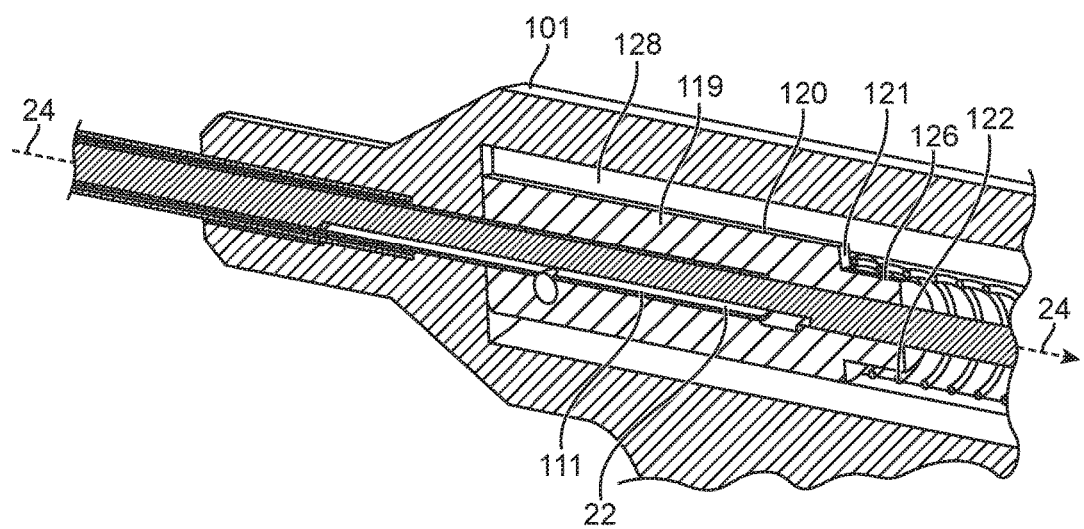
FIG. 5B illustrates a cross-sectional view of the needle demonstrating the inner workings of a needle handle.

Cross sectional views of the preferred embodiment of the needle 100 are shown in FIGS. 5A and 5B that illustrate the inner workings of the handle 101. A proximal portion 22 of the obturator tube 111 may be connected to an obturator hub 119. The hub 119 may have one or more rotational alignment structures such as a flat face 120 or an alignment post 121 that prevent the hub 119 from rotating about a long axis 24 as it translates back and forth. Additional extrusions 128 inside the housing 101 may be necessary to mate with the alignment protrusions 120, 121 on the hub 119. The alignment of the hub 119 is critical to ensure the cutout 113 at the distal end maintains its alignment for suture capturing. The hub 119 may also have a cylindrical portion 126 to accommodate a coil spring 122 that is used to spring load the obturator tube 111. The opposing end of the spring 122 may connect to the actuator 105 at a similarly accommodating cylindrical portion 127. The capture rod 114 may be attached to the actuator 105 with a pin 123 that passes through a hole 124 in the actuator and a slot 129 in the capture rod. As previously described, the pin 123 may slide within a window 104 of the housing 101 that is used to limit the travel and prevent rotation of the capture rod 114.

Figure 6C:
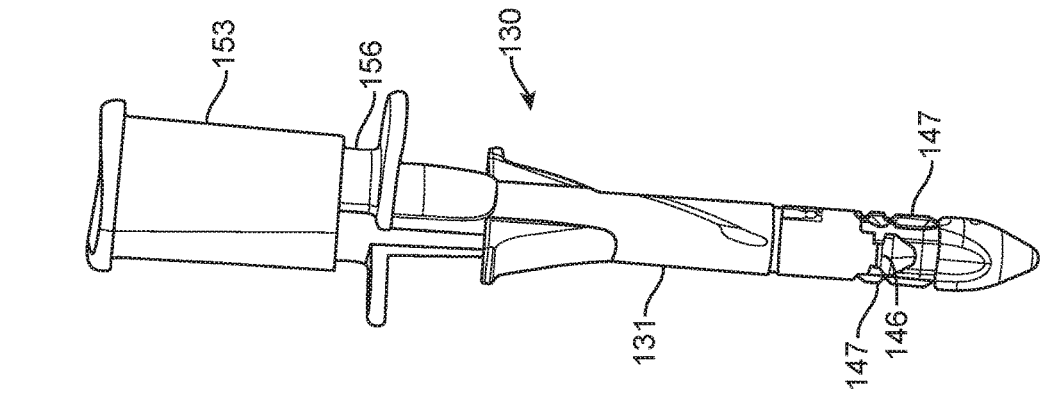
FIG. 6C illustrates an oblique view of the guide with radially contracted arms and snare loops.
Figure 6B:
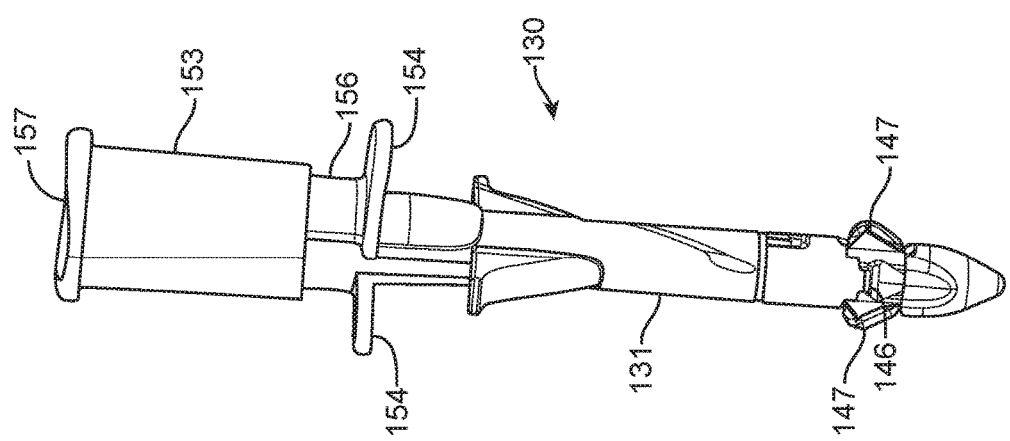
FIG. 6B illustrates an oblique view of the guide with radially expanded arms and contracted snare loops.
Figure 6A:
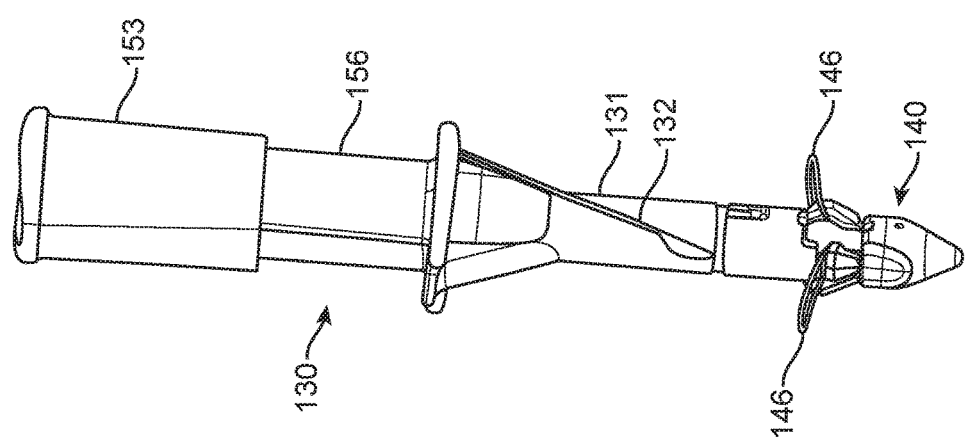
FIG. 6A illustrates an oblique view of the guide with radially expanded arms and snare loops.

In FIGS. 6A-6C, a preferred embodiment of a guide 130 may be useful for directing the above described suture engaging device through a body wall. The guide 130 may be particularly useful for the placement of sutures used in closing wounds or openings through body walls made in surgical procedures to access internal body cavities. Accordingly, the guide 130 preferably comprises two pathways diagonal to each other and oriented to direct a needle apparatus to both a first internal location to carry and release a first end of a suture, and a second internal location to carry and release a second end of a suture.

Figure 12:
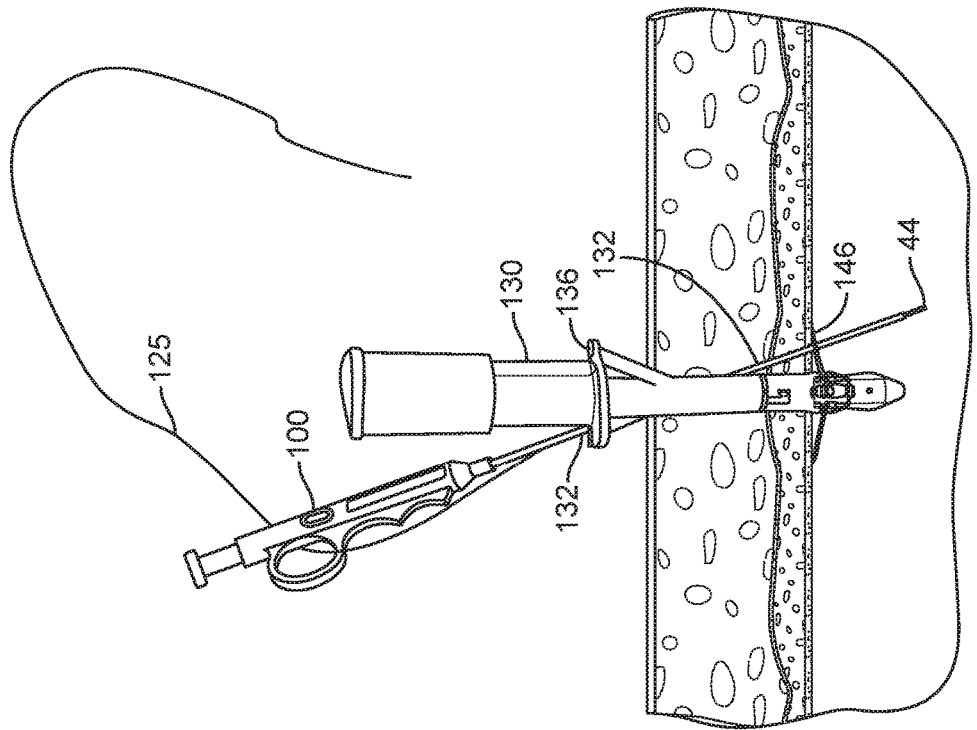
FIG. 12 illustrates a perspective side view of the insertion of the needle with first end of suture strand into the guide.

An oblique view of the preferred guide 130 is shown in FIGS. 6A-6C. The guide 130 may comprise a distal barrel tip 140 with two radially expanding arms 147, two suture snare loops 146, a main barrel 131 with two channels 132, 136 (shown in FIG. 8), a plunger 153, and a slider 156. The two channels 132, 136 are disposed within the main barrel 131 to guide the suture passing needle 100 through the tissue to be sutured, as shown in FIGS. 8 and 12. The slider 156 may be slidably disposed onto the main barrel 131 to provide actuation of the suture snare loops 146. The plunger 153 may be slidably disposed onto the main barrel 131 to provide actuation of the expanding arms 147. The expanding arms 147 may serve as an internal cavity securing mechanism, which is used to secure the guide 130 against the internal peritoneal wall. The two suture snare loops 146 serve the purpose of capturing the suture material after it has been passed through the tissue wall by inwardly retracting both snare loops 146 without lengthening the distal tip 140 with respect to the barrel 131, without twisting or rotating the snare loops 146, and without embedding or entangling the suture portions inserted through the two openings. As shown in FIGS. 6A, 6B, 7 and 8, the two snare loops 146 are clearly not composed of mesh or bows, and thus are not surrounded by any other suture snaring structures or mechanisms. Since both self-supporting snare loops 146 hold their shape in the radially extended configuration shown in FIG. 6A, the snare loops 146 are clearly not acting in the capacity as a suture, but are instead distinct and separate from the suture portions being captured by the snare loops 146. The slider 156 may facilitate the ease of handling of the guide 130.

Figure 13B:
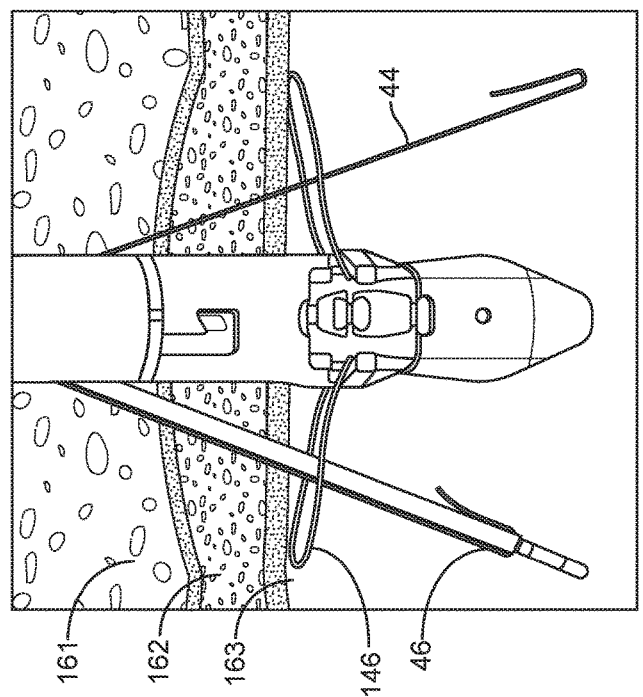
FIG. 13B illustrates a perspective side view of an enlarged view of the insertion of the needle with second end of suture strand into the guide.
Figure 13A:
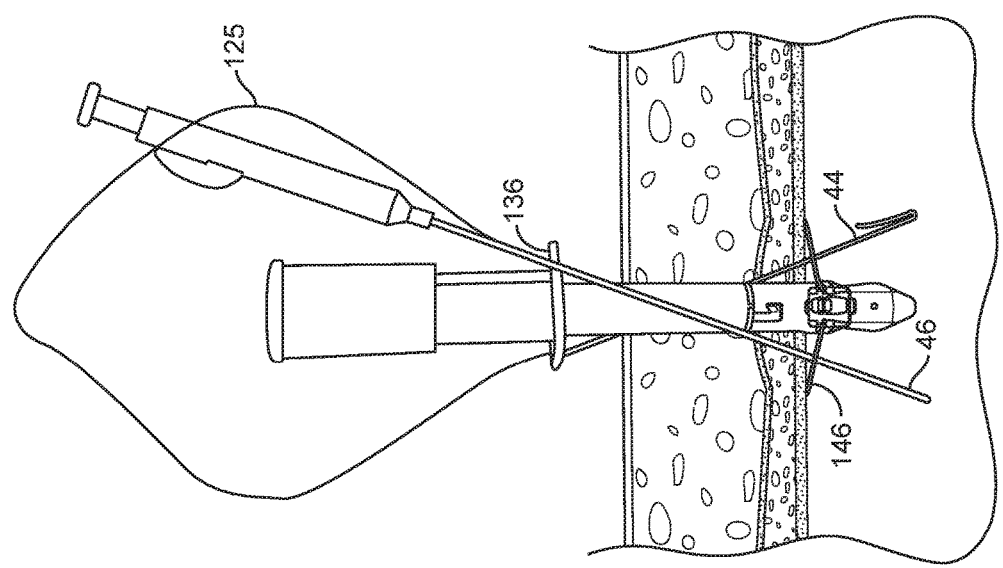
FIG. 13A illustrates a perspective side view of the insertion of the needle with second end of suture strand into the guide.

As the slider 156 translates with respect to the barrel 131, the suture snare loops 146 move between two positions of radially extended shown in FIG. 6A and retracted shown in FIG. 6B without the distal tip 140 shortening or lengthening with respect to the barrel 131. Unlike accordion style suture retrieval mechanisms, the distal tip of the guide 140 does not axially shorten with respect to the barrel 131 when the snare loops 146 are moved toward and held in the radially extended configuration shown in FIG. 6A. When each snare 146 is in the radially extended configuration, a loop, ring, circle or hoop shape is preferably formed. Each snare loop 146 provides an unencumbered opening or region for a suture passing needle to pass into and drop off the suture without the needle or carried suture portions contacting the snare loop 146. Each snare loop 146 defines an opening through which the carried suture traverses without getting embedded or entangled by the snare loop 146 or any other surrounding structure as shown in FIGS. 13A and 13B. When the carried suture is released from the suture engaging device, the suture section intersecting the opening of the snare loop 146 resides loosely until the snare loop 146 is retracted. When the snare loop 146 is retracted the suture material becomes trapped between the snare loop 146 and the wall of the distal barrel tip 140.

Further, as the plunger 153 translates with respect to the barrel 131, the radially expanding arms 147 at the distal barrel tip 140 move between two positions of radially expanded, or flared out, as shown in FIG. 6B, and radially contracted, or slender, as shown in FIG. 6C. Each of the expanding arms 147 preferably comprise a living hinge section, where the material is cut thin at specific locations allowing for the material to flex. It is to be expressly understood that the expanding arms may comprise a variety of structures and mechanisms that are capable of moving between slender and flared out configurations.

As shown in FIG. 7, radially adjacent to the expanding arms 147 may be one or more distally extending stop tabs 143. The stop tabs 143 are configured to provide a mechanical stop for the distal end cap 141 of the barrel tip 140 to collide against preventing excessive flex within the thin sections 148, 149, 150 of the expanding arms 147. The stop tabs 143 may also have a slot 145 cutout in the outer wall that provide a region for the snare loop material 146 to be housed when the snare loop 146 is in the retracted state. When a section of suture 159 is captured within the snare loop 146, the slot 145 may provide additional security to the captured suture 159, as opposed to the snare loop 146 pulling the suture against a smooth surface.

The barrel tip 140 may comprise a separate component that is assembled to the main barrel 131. Two tabs 166 on the main barrel 131 may be placed radially opposite to each other. Slots 167 in the barrel tip 140 may allow for the tip 140 to initially slide past the tabs 166 on the main barrel 131. The slots 167 may have an undercut section 168 that may be engaged by rotating the tip 140 and pulling it distally. The gap that is created between the tip 140 and the barrel 131 may be filled with a deformable c-shaped clip 169 to prevent the tip 140 from dislodging from the barrel 131.

The slider 156 is slidably disposed on the main barrel 131 as it can travel between a distal position shown in FIG. 6A and a proximal position shown in FIG. 6B. Two finger tabs 154 are preferably disposed near the distal end of the slider 156 and configured to be grasped with one or more fingers. The thumb or palm of the hand may then be pressed against the proximal face 157 of the plunger 153. The finger tabs 154 may then be pulled proximally to actuate the guide 130 with the plunger 153 being used to provide a counterforce. The slider 156 can reach a stop, achieved by either an internal feature of the slider 156 engaging the main barrel 131 or the snare loops 146 being fully retracted. Additional force between the slider 156 and the plunger 153 may overcome the counterforce translated to the plunger 153 by a spring. The plunger 153 can then move axially to actuate the expanding arms 147 to the slender contracted state. Upon release of the force between the slider 156 and the plunger 153, the plunger 153 can return to the original position and result in the expanding arms 147 reverting to the radially expanded position. The slider 156 may be biased to the distal position by a spring that passively returns the slider 156 to the distal position when released, thus resulting in the suture loops 146 reverting back to the radially extended position. It may be appreciated that biasing the guide 130 in this configuration may allow for the surgeon to have his hands free from operating the guide 130 such that work with other instruments may be conducted once the guide 130 has been inserted into the trocar wound.

In the preferred embodiment, the guide 130 provides two different, diagonal pathways for a suture passing needle apparatus and thus comprises first and second channels 132, 136 as more clearly shown in FIG. 8. The channels 132, 136 are directionally diagonal to the long axis "24" of the guide 130 at some acute angle, preferably in the range of 5-30 degrees. The angle of the channels 132, 136 controls the depth of bite into the tissue, such that a greater angle provides a greater bite of tissue. Angular spacing between entries to the channels 132, 136 are preferably equal (i.e., equiangular) depending upon the number of channels, e.g., 180 degrees apart if there are two channels, 120 degrees apart if there are three channels, etc. Two separate entry points 133, 137 are provided on the channels 132, 136 for a suture passing needle to enter the guide 130, as well as two separate exit points 134, 138. Each channel 132, 136 has a slot 135, 139, or opening that allows for a strand of suture to be removed from the channel. This may be necessary to complete the suture loop in the tissue.

Figure 9A:
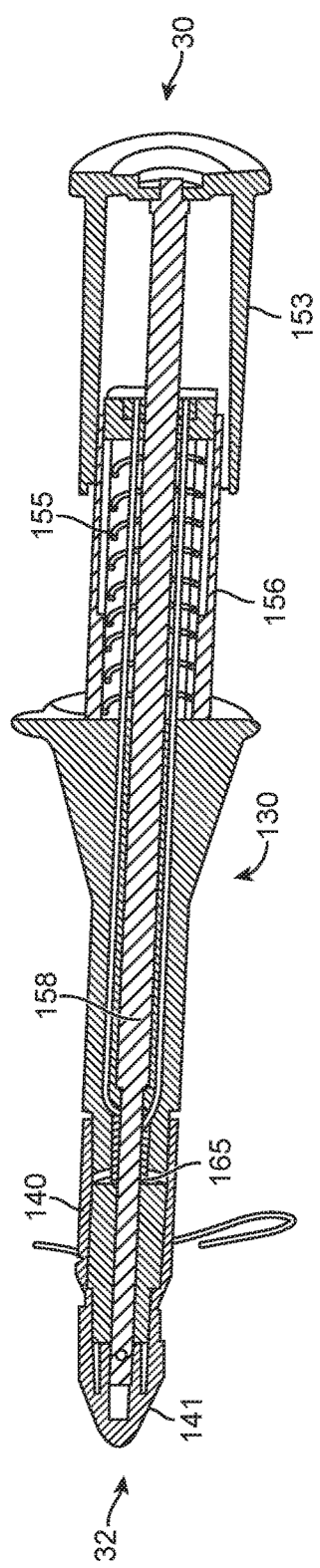
FIG. 9A illustrates a cross-sectional view of the guide showing internal components.
Figure 9B:
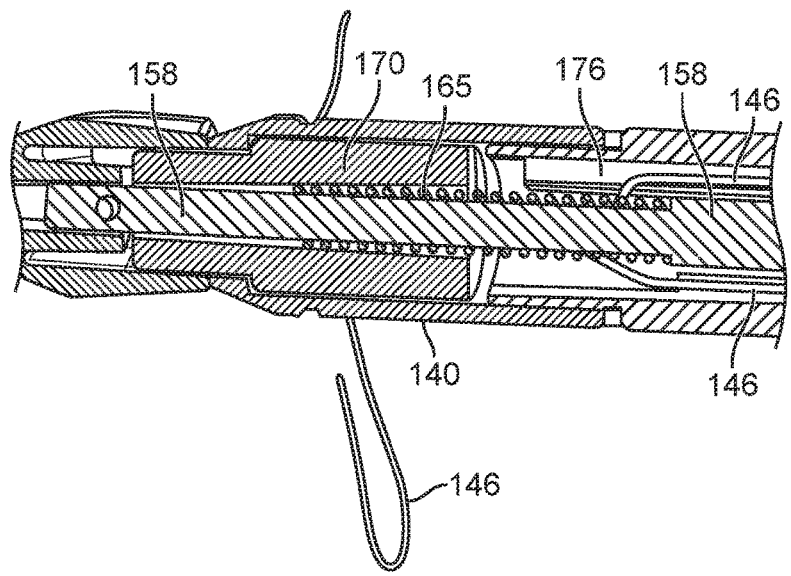
FIG. 9B illustrates an enlarged cross-sectional view of the guide showing distal internal components.
Figure 9C:
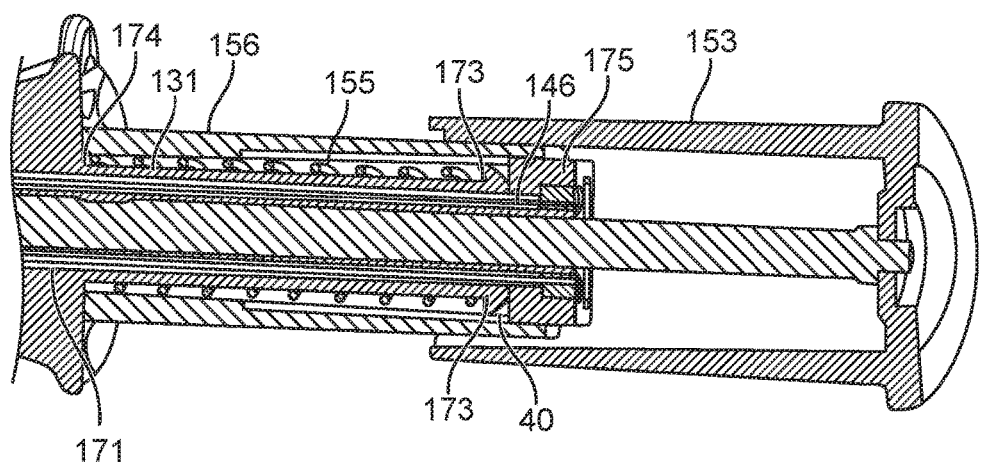
FIG. 9C illustrates an enlarged cross-sectional view of the guide showing proximal internal components.

The internal workings of the guide 130 are shown in FIGS. 9A-9C, which illustrate cross-sectional views through the center of the guide 130. An inner shaft 158 spans from the proximal end 30 to the distal end 32 of the guide 130 and is used to actuate the expanding arms 147. The shaft 158 connects at the distal end 32 of the guide 130 to the distal end cap 141 of the barrel tip 140, and connects at the proximal end 30 of the guide 130 to the plunger 153. A retaining ring, heat stake, or other mechanical fastening means may be used to secure the shaft 158 to the plunger 153. When the slider 156 is pulled into the proximal position as shown in FIG. 6B, a counterforce is applied to the plunger 153. Upon the slider 156 reaching the full proximal extension, further pushing on the plunger 153 advances the shaft 158 distally which in turn advances the end cap 141 on the barrel tip 140 distally, causing the expanding arms 147 to radially contract as shown in FIG. 6C. Upon release of the plunger 153 and slider 156, the shaft 158 may passively return to its native proximal position, pulling the end cap 141 with it and causing the expanding arms 147 to radially extend.

Two springs are used to bias the guide 130 into the configurations shown in FIGS. 6A and 9A, with the radially extended arms 147 and snare loop 146 expanded, and the plunger 153 in the proximal position. A slider spring 155 is used to bias the slider 156 to the proximal position. In FIG. 9C, one end of the slider spring 155 is captured at the proximal end 40 of the main barrel 131 by two spring capture tabs 173. The opposing end of the spring 155 rests against an inner edge 174 of the slider 156, forcing the slider 156 to a proximal position. In FIG. 9B, a plunger spring 165 is used to bias the distal barrel tip 140 in the proximal position. The spring 165 is captured between inner shaft 158 and the proximal face of track support 170 connected to the barrel tip 140. This plunger spring 165 forces the inner shaft 158 and plunger 153 in a proximal position, pulling the barrel tip 140 proximally as well.

In FIG. 9C, the free ends of a snare cord loop 146 may be captured in a retaining cap 175 that is fixed to the proximal end of the slider 156. The snare cord 146 may traverse distally down the guide 130 either through snare channels 176 inside the main barrel 131 or guide tubes 171 that span through a portion of the length of the main barrel 131. The snare channels 176 or guide tubes 171 may be used to constrain the snare cord material 146 and prevent it from bunching up or buckling under load as it travels proximally and distally within the guide 130.

FIGS. 10A-10B illustrate the laminate component construct that provides tracks 172 within the barrel tip 140. The track support 170 is positioned between two track side panels 177. The tracks 172 may be used to guide the snare cord 146 from a position within the barrel tip 140, parallel to the long axis of the guide 130 to a position exiting the barrel tip 140 relatively perpendicular to a long axis 42 of the guide 130. These curved exit tracks 172 may take on an angulation of approximately 90 degrees, however this angle may be made more acute or obtuse to optimize the positioning of the snare.

Figure 11:
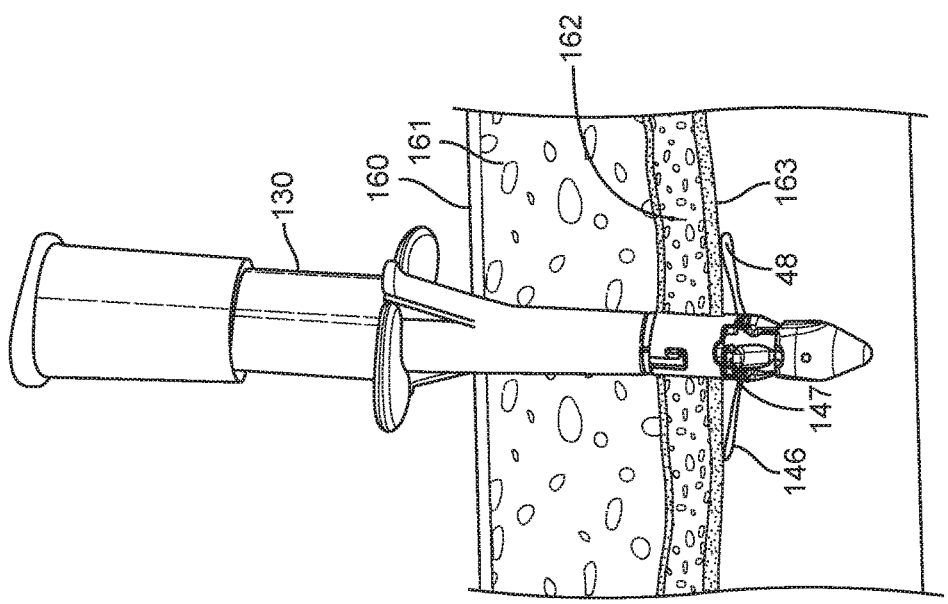
FIG. 11 illustrates a perspective side view of the insertion of guide into tissue.

In the case of a laparoscopic surgery involving use of a trocar, the guide 130 may be placed through the tissue layers of the open trocar wound site as shown in FIG. 11. This tissue track may consist of skin 160, adipose tissue 161, muscle and fascia 162 and the peritoneum 163. Prior to insertion of the guide 130 through the tissue track, the slider 156 and plunger 153 may be pulled into the compressed position to place the arms 147 in the slender configuration, and the snare loops 146 in the retracted position. Once the distal barrel tip 140 of the guide 130 is appropriately placed posterior to the peritoneal layer 163, the slider 156 and plunger 153 may be released and spring-biased to the open position, extending the suture snare loops 146 and expanding the tissue engaging arms 147. The guide 130 may then be retracted until the tissue engaging arms 147 are resting against the inner peritoneal wall 163 to align the channels 132, 136 with the appropriate layers of tissue to be sutured.

Once the guide 130 is secured against the peritoneal wall 163, the suture engaging device 100, with a first free end section 44 of suture 125 engaged, may be inserted through a channel 132 while carrying the section 44 of suture 125, as shown in FIG. 12. Once the needle 100 exits the channel 132 it passes through various layers of tissue 162, 163 and enters the body cavity. As it enters the body cavity, the needle 100 passes through the snare loop 146. The needle 100 may release the strand of suture 125 and be removed from the body leaving the suture section 44 loosely inside the expanded snare loop 146. Thus, the suture section 44 is carried into the body cavity to a point where the suture section 44 intersects and traverses the generally planar opening 48 (see FIG. 11) defined by the expanded snare loop 46.

The second free end section 46 of suture 125 may then be engaged by the suture engaging device 100, and inserted through the opposing channel 136 to place the second end suture section 46. As shown in FIGS. 13A-13B, once the needle 100 exits the channel 136 it passes through various layers of tissue 162, 163 and enters the body cavity. As it enters the body cavity, the needle 100 passes through the opposing snare loop 146 without the needle 100 or carried suture 46 contacting the snare loop 146. The needle 100 may release the strand of suture 125 and be removed from the body leaving the suture sections 44, 46 within the boundaries of the respective snare loops 146. As shown in FIG. 13B, the carried and released suture portions 44, 46 reside loosely within the respective openings of the two snare loops 146 without being embedded or entangled by any other suture retrieving mechanism.

Figure 13C:
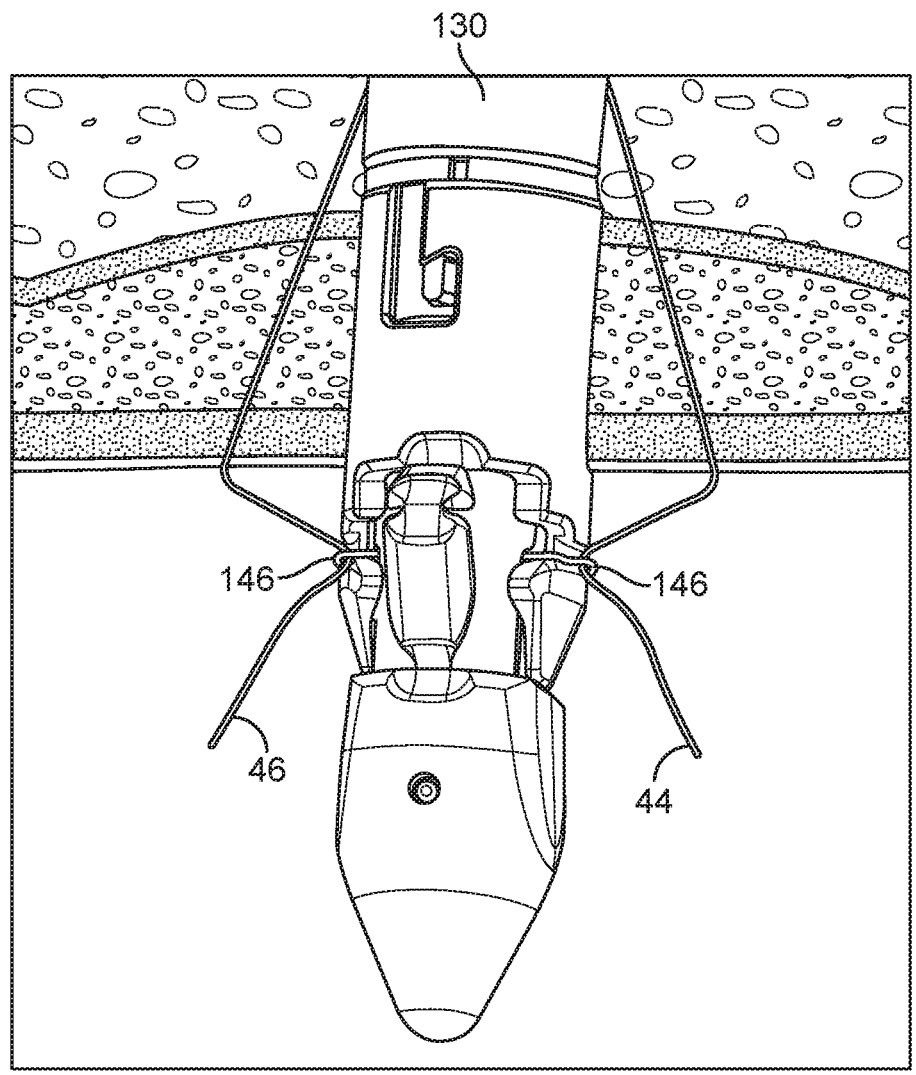
FIG. 13C illustrates a perspective side view of the guide with the snare loops retracted so as to capture the suture sections.
Figure 13D:
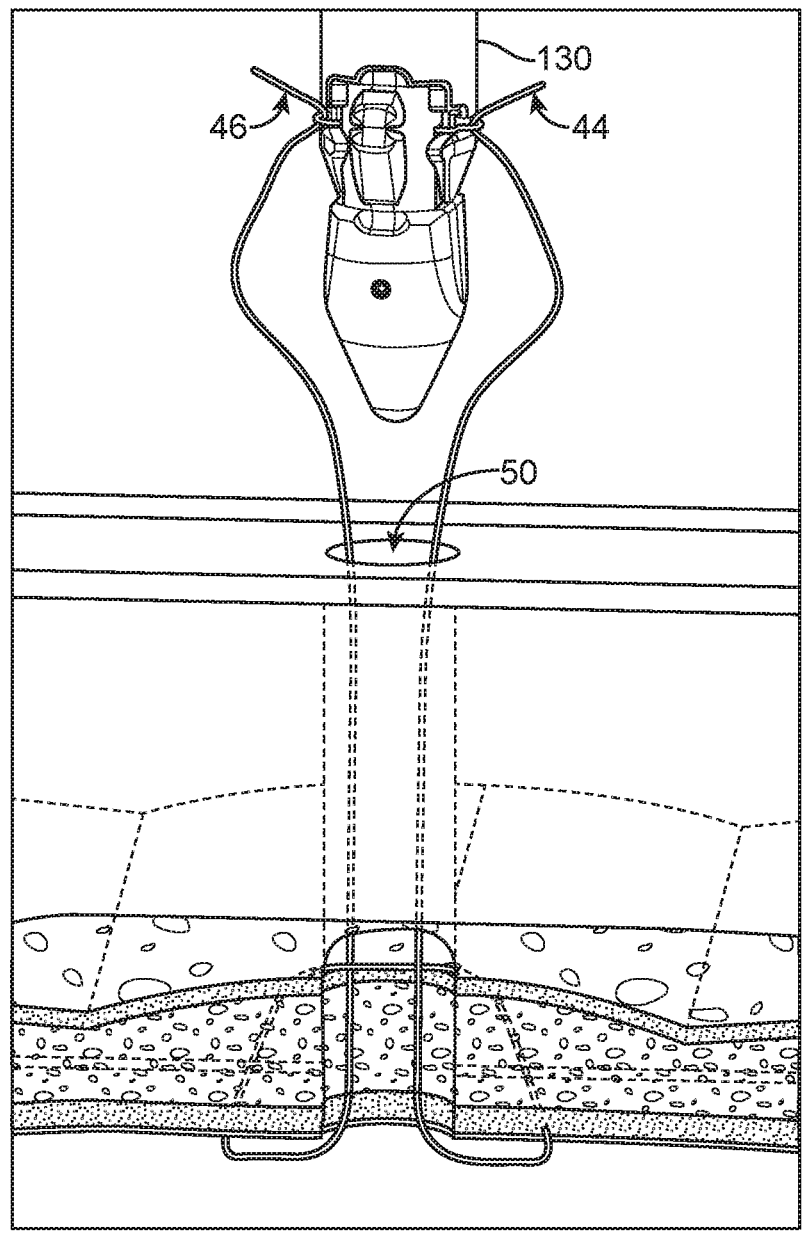
FIG. 13D illustrates a perspective side view of the guide retracted out from the tissue track with the captured suture sections.

FIG. 13C shows the snare loops 146 retracted so as to close the respective openings and simultaneously capture the suture sections 44, 46, which is the configuration actuated in FIG. 6B when the slider 156 is moved proximally with respect to the main barrel 131. With both suture sections 44, 46 captured by virtue of retraction of the snare loops 146 that occurs without any twisting or rotating, the guide 130 is ready to be retracted from the tissue track 50, carrying the suture sections 44, 46 as shown in FIG. 13D.

Figure 14:
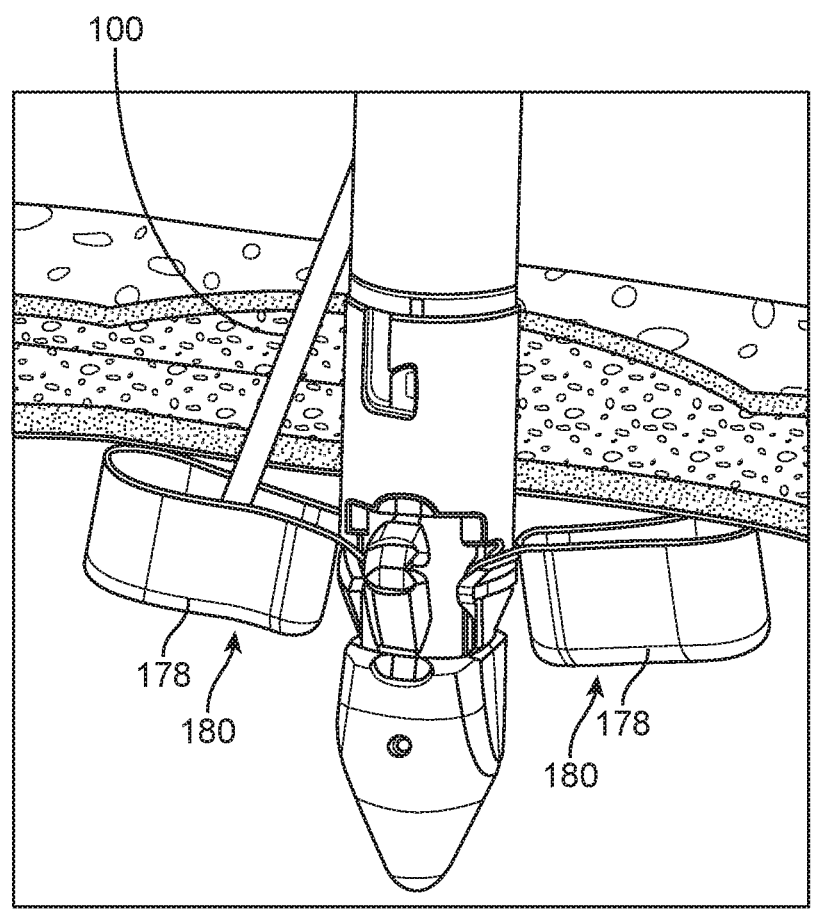
FIG. 14 illustrates an isometric view of snare with protective basket.

FIG. 14 illustrates an alternative embodiment including a pouch, or basket, 178 secured to the snare. The pouch 178 is positioned below the snare and comprises a floor 180 as a protective element to prevent the distal tip of the needle 100 from extending deeper into the abdominal cavity. The pouch may be constructed of a compliant fabric, rigid polymer, or other such material to obstruct needle penetration.

Figure 15:
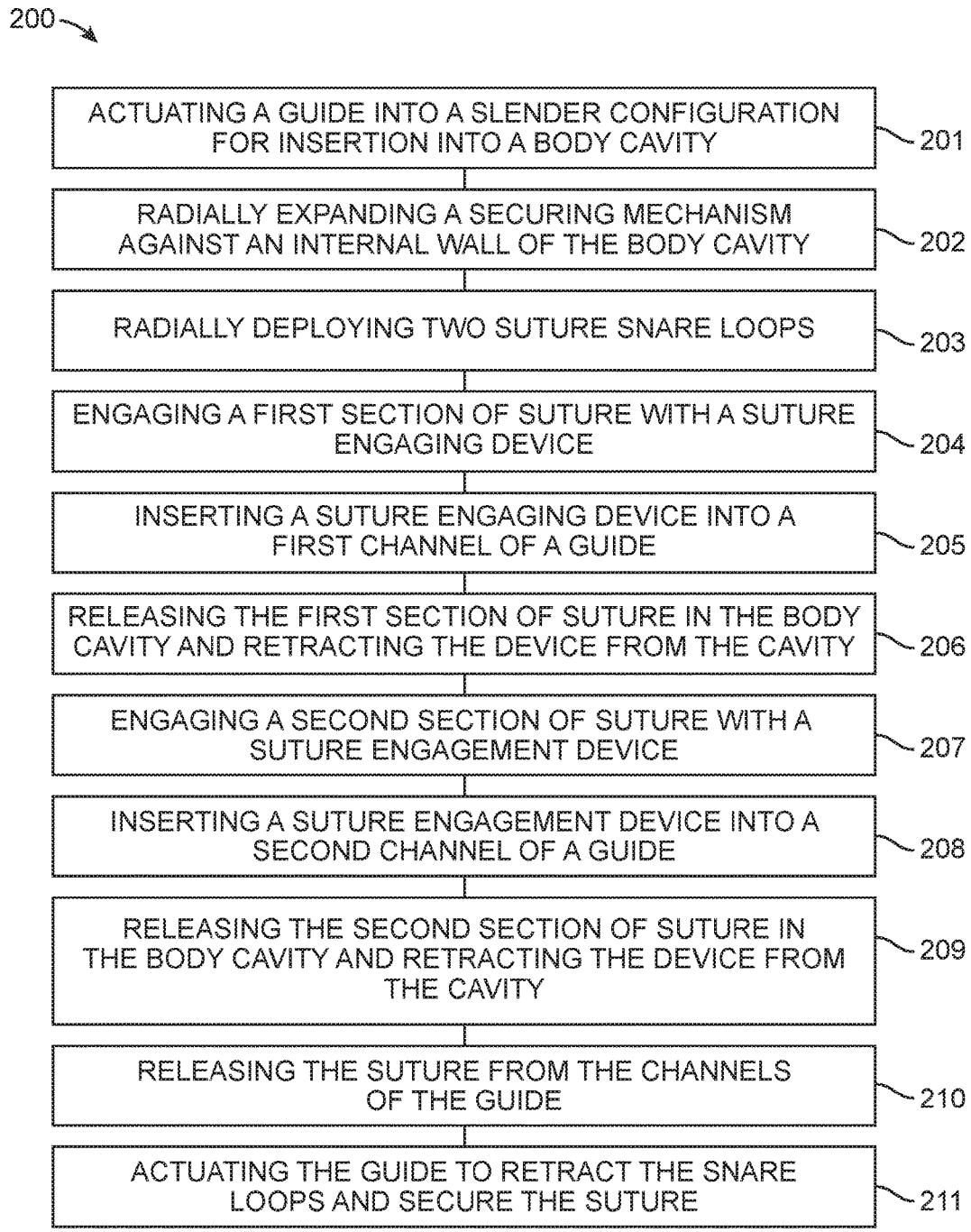
FIG. 15 illustrates a preferred method for closing a surgical wound with a single stitch using a system comprising preferred embodiments of a guide and a suture engaging device disclosed above.
Figure 15:
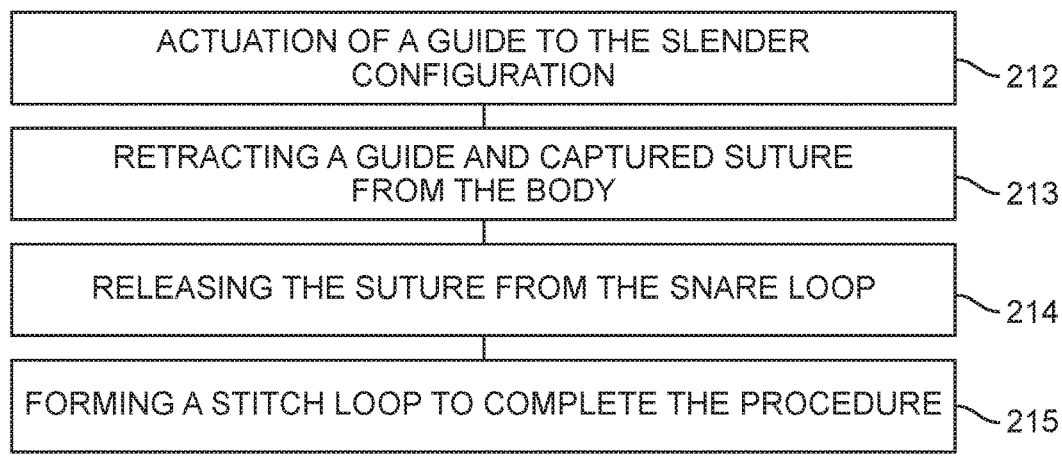

In FIG. 15 a preferred method 200 is disclosed for closing a surgical wound using a surgical instrumentation system comprising a guide and suture engagement device as described above. It will be appreciated that this method 200 enables an operator to pass and retrieve the suture using simply a guide and suture engaging device without the need for additional instrumentation or visualization inside the body cavity. The initial step 201 comprises actuation of the guide into a slender configuration and insertion of the distal tip into the surgical wound. In step 202, a securing mechanism, which may comprise living hinges, is radially expanded for engagement with the inner body cavity wall when the guide is retracted, preventing the guide from being pulled out of the wound as well as providing a reference point for the suture placement. Step 203 comprises the deployment of two snare loops to be used to capture the suture material. It can be appreciated that step 202 and 203 may be combined such that they occur simultaneously. It will further be appreciated that steps 202 and 203 may occur by default (e.g., through use of springs) upon release of the guide such that the operator may have both hands free to engage other instruments.

Step 204 comprises engaging and capturing a first section of a suture with a suture capture mechanism disposed at the distal end of a suture engaging device having a shaft. In step 205 the suture engaging device with secured suture is inserted through a first track of the guide, through various tissue layers, and ultimately ending inside the body cavity as it passes through the first snare loop. Step 206 comprises releasing the first suture section from the suture engaging device and retracting the device from the body and guide. The first section of the suture may remain inside the body cavity and loosely encapsulated within the boundaries of the expanded first snare loop.

Step 207 comprises engaging and capturing a second section of the same suture with the suture capture feature on the suture engaging device. In step 208, the suture engaging device with secured suture is inserted through a second track of the guide, through various tissue layers, ending inside the body cavity as it passes through the second snare loop. Step 209 comprises releasing the suture from the suture engaging device and retracting the device from the body and guide while leaving the second section of the suture inside the body cavity and loosely encapsulated within the boundaries of the second snare loop.

In step 210, the suture material may be passed through the slots in the channels on the guide to release the suture from the constraint of the channel. Step 210 comprises retracting the snare loops back against the guide and securing the suture between the outer guide wall and the snare loop. In step 211, the guide may be actuated such that the securing mechanism is radially contracted and converting the guide into the slender configuration. It can be appreciated that step 210 and 211 may be combined such that they occur simultaneously or seamlessly with a single motion. In step 213 the guide can be removed from the body cavity with the two captured sections of the suture. Step 214 comprises releasing the suture from the snare loops on the guide.

The procedure may then be completed at step 215 by forming a single stitch loop to close the surgical wound.

Figure 16:
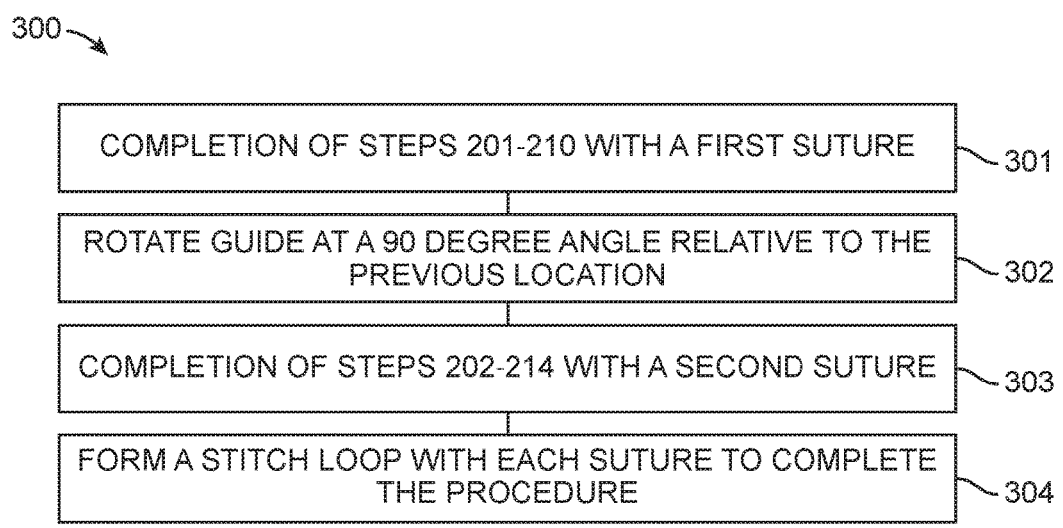
FIG. 16 illustrates a preferred method for closing a surgical wound with a figure eight stitch using the preferred system disclosed above.

In FIG. 16 an alternative method 300 is illustrated for closing a surgical wound using a surgical instrumentation system by forming a figure eight stitch as opposed to the single stitch method 200. In step 301 a first length of suture is passed into the body at a first location of the wound comprising the same steps 201-210 as previously described. In step 302, the guide is rotated 90 degrees from the initial position in step 301. In step 303, a second length of suture is passed into the wound at a second location of the wound comprising steps 202-214. Step 304 comprises completing the closing of the wound by forming a stitch loop with each of the suture strands.

Figure 17:
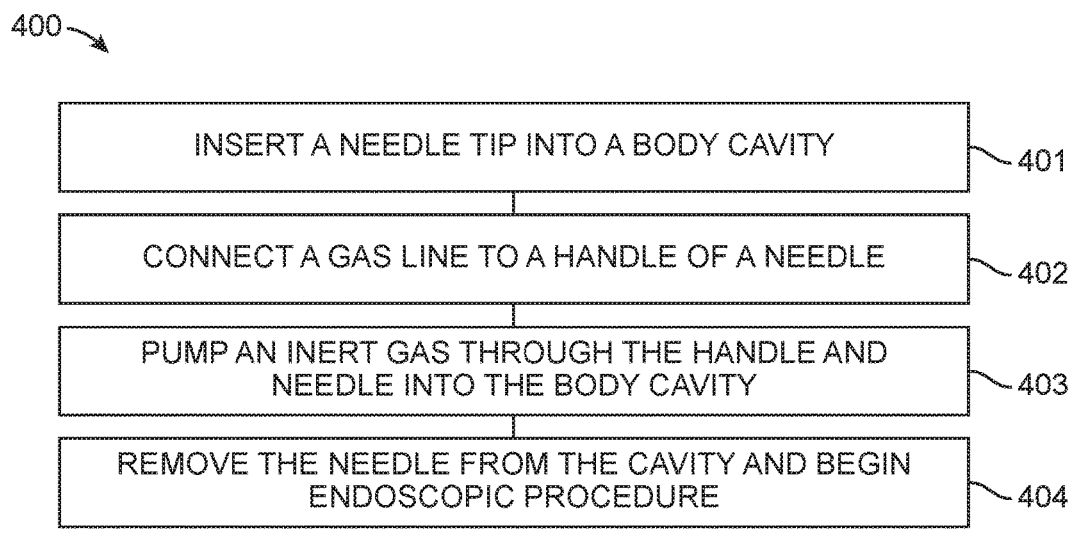
FIG. 17 illustrates a preferred method for creating pneumoperitoneum for laparoscopic procedures using an insufflation needle.

In FIG. 17 a preferred method 400 is illustrated for creating pneumoperitoneum for laparoscopic procedures using an insufflation needle. Step 401 comprises inserting the tip of the needle through the abdominal wall and into a body cavity. This step may also initially require a small incision in the skin to be made prior to insertion of the needle. In step 402, a gas line may be connected to the needle. Step 403 comprises pumping an inert gas through the needle and into the body cavity until an appropriate internal pressure is achieved. Lastly, in step 404 the needle may be removed from the body and the endoscopic procedure can begin.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements. The claims are thus to be understood to include what is specifically illustrated and described above, what is conceptually equivalent, what can be obviously substituted and also what incorporates the essential idea of the invention.

What is claimed is:

1. A surgical guide device to be placed through a tissue track, comprising:
  a barrel defining a first channel and a second channel, the first channel comprising a first exit for directing a first suture portion into a body cavity, the second channel comprising a second exit for directing a second suture portion into the body cavity;
  a distal tip located distally to the barrel and comprising a distal tip wall;
  a first self-supporting snare loop positioned adjacent to the first exit;
  a second self-supporting snare loop positioned adjacent to the second exit; and
  an actuator coupled to the first and second snare loops, the actuator being configured to move the first and second snare loops in unison between a radially extended configuration and a retracted configuration, wherein, in the radially extended configuration, the first self-supporting snare loop defines a first unencumbered opening through which the first suture portion intersects the opening and then resides loosely within the first opening, and
  wherein, in the radially extended configuration, the second self-supporting snare loop defines a second unencumbered opening through which the second suture portion intersects the opening and then resides loosely within the second opening,
  wherein the first and second self-supporting snare loops are apart from one another, and
  wherein the first self-supporting snare loop and the second self-supporting snare loop exit radially outward and in opposite directions from the distal tip.

2. The device of claim 1, wherein, in the radially extended configuration, the first self-supporting snare loop does not embed the first suture portion and the second self-supporting snare loop does not embed the second suture portion.

3. The device of claim 1, wherein the first self-supporting snare loop and the second self-supporting snare loop are detached and separate from any sharp needles.

4. The device of claim 1, wherein:
  the actuator moves proximally with respect to the barrel to move the first and second self-supporting snare loops in unison to the retracted configuration; and the actuator moves distally with respect to the barrel to move the first and second self-supporting snare loops in unison to the radially extended configuration.

5. The device of claim 1,
wherein the first self-supporting snare loop and the second self-supporting snare loop exit radially outward and in opposite directions from the distal tip without the distal tip axially shortening with respect to the barrel when changing between the retracted configuration and the radially extended configuration.

6. The device of claim 1, wherein the first self-supporting snare loop and the second self-supporting snare loop are detached and separate from any sharp needles.

7. The device of claim 1, wherein retraction of the first self-supporting snare loop and the second self-supporting snare loop in unison closes the first opening and the second opening while simultaneously capturing the first suture portion and the second suture portion.

8. The device of claim 1, wherein:
the first self-supporting snare loop in the radially extended configuration forms the first opening with a first region into which a needle passes and drops the first suture portion such that the first suture portion resides loosely within the first opening; and
the second self-supporting snare loop in the radially extended configuration provides the second opening with a second region sufficiently large into which the needle passes and drops the second suture portion such that the second suture portion resides loosely.

9. The device of claim 1, wherein:
the first self-supporting snare loop in the radially extended configuration forms the first opening with a first region into which a first needle passes and drops the first suture portion such that the first suture portion resides loosely within the first opening; and
the second self-supporting snare loop in the radially extended configuration provides the second opening with a second region sufficiently large into which a second needle passes and drops the second suture portion such that the second suture portion resides loosely.

10. A surgical guide device to be placed through a tissue track, comprising:
a barrel defining a long axis, a first channel and a second channel, the first channel comprising a first exit for directing a first suture portion into a body cavity, the second channel comprising a second exit for directing a second suture portion into the body cavity;
a distal tip located distally to the barrel and comprising a distal tip wall;
a first self-supporting snare loop positioned adjacent to the first exit;
a second self-supporting snare loop positioned adjacent to the second exit; and
an actuator coupled to the first and second self-supporting snare loops, the actuator being configured to move the first and second self-supporting snare loops in unison between a radially extended configuration and a retracted configuration,
wherein the distal tip does not shorten with respect to the barrel along the long axis when the first and second self-supporting snare loops are moved in unison between the radially extended configuration and the retracted configuration,
wherein the first self-supporting snare loop in the radially extended configuration defines a first boundary within which a first suture portion resides loosely and the second self-supporting snare loop in the radially extended configuration defines a second boundary within which a second suture portion resides loosely,
wherein the first and second self-supporting snare loops trap in unison the first and second suture portions, respectively, against the distal tip wall when the first and second self-supporting snare loops are retracted in unison, and
wherein the first self-supporting snare loop and the second self-supporting snare loop exit radially outward and in opposite directions from the distal tip.

11. The device of claim 10, wherein, in the radially extended configuration, the first suture portion resides loosely in the first self-supporting snare loop and the second suture portion resides loosely in the second self-supporting snare loop.

12. The device of claim 10, wherein the first self-supporting snare loop and the second self-supporting snare loop are detached and separate from any sharp needles.

13. The device of claim 10, wherein:
the actuator moves proximally with respect to the barrel to move the first and second self-supporting snare loops in unison to the retracted configuration; and
the actuator moves distally with respect to the barrel to move the first and second self-supporting snare loops in unison to the radially extended configuration.

14. The device of claim 10, wherein retraction of the first self-supporting snare loop and the second self-supporting snare loop in unison closes the first opening and the second opening while simultaneously capturing the first suture portion and the second suture portion.

15. The device of claim 10, wherein, in the radially extended configuration, only two distinct loops extend from the distal tip of the barrel, the two distinct loops forming the first and second self-supporting snare loops.

16. A surgical guide device to be placed through a tissue track, comprising:
a barrel defining a first channel and a second channel, the first channel comprising a first exit for directing a first suture portion into a body cavity, the second channel comprising a second exit for directing a second suture portion into the body cavity;
a distal tip located distally to the barrel and comprising a distal tip wall;
a first self-supporting snare loop positioned adjacent to the first exit;
a second self-supporting snare loop positioned adjacent to the second exit; and
an actuator coupled to the first and second snare loops, the actuator being configured to move the first and second snare loops in unison between a radially extended configuration and a retracted configuration,
wherein, in the radially extend configuration, the first self-supporting snare loop defines a first opening through which the first suture portion resides loosely upon release,
wherein, in the radially extended configuration, the second self-supporting snare loop defines a second opening through which the second suture portion resides loosely,
wherein, in the radially extended configuration when the surgical guide device is positioned through the tissue track, the body cavity on a first side of the barrel has the first self-supporting snare loop and the body cavity on a second side of the barrel has the second self-supporting snare loop, only two distinct loops extend from a distal tip of the barrel, the two distinct loops forming the first and second self-supporting snare loops and wherein retraction of the first and second self-supporting snare loops in unison closes the first and second openings while simultaneously capturing the first and second suture portions by trapping the first and second suture portions without rotating the first and second self-supporting snare loops, wherein the first and second self-supporting snare loops are apart from each other, and wherein the first self-supporting snare loop and the second self-supporting snare loop exit radially outward and in opposite directions from the distal tip.

17. The device of claim 16, wherein the first self-supporting snare loop and the second self-supporting snare loop are detached and separate from any sharp needles.

18. The device of claim 16, wherein:
the actuator moves proximally with respect to the barrel to move the first and second self-supporting snare loops in unison to the retracted configuration; and
the actuator moves distally with respect to the barrel to move the first and second self-supporting snare loops in unison to the radially extended configuration.

19. The device of claim 16,
wherein the first self-supporting snare loop and the second self-supporting snare loop exit radially outward and in opposite directions from the distal tip without the distal tip axially shortening with respect to the barrel when changing between the retracted configuration and the radially extended configuration.

20. The device of claim 16, wherein retraction of the first self-supporting snare loop and the second self-supporting snare loop in unison closes the first opening and the second opening while simultaneously capturing the first suture portion and the second suture portion.

21. The device of claim 16, wherein, in the radially extended configuration, only two distinct loops extend from the distal tip of the barrel, the two distinct loops forming the first and second self-supporting snare loops.

22. A surgical guide device to be placed through a tissue track, comprising:
a needle for passing suture,
a barrel defining a first channel and a second channel, the first channel comprising a first exit for directing a first suture portion into a body cavity, the second channel comprising a second exit for directing a second suture portion into the body cavity;
a first self-supporting snare loop positioned adjacent to the first exit;
a second self-supporting snare loop positioned adjacent to the second exit;
a distal tip located distally to the barrel and comprising a distal tip wall; and
an actuator coupled to the first and second snare loops, where the first and second snare loops extend from the actuator, the actuator being configured to move the first and second snare loops in unison between a radially extended configuration and a retracted configuration, wherein, in the radially extended configuration, the first self-supporting snare loop defines a first opening, and
wherein, in the radially extended configuration, the second self-supporting snare loop defines a second opening through which the second suture portion resides loosely within the second opening, and
wherein the first and second self-supporting snare loops are apart from each other, and
wherein the first self-supporting snare loop and the second self-supporting snare loop exit radially outward and in opposite directions from the distal tip.

23. The device of claim 22, wherein the first self-supporting snare loop and the second self-supporting snare loop are detached and separate from any sharp needles.

24. The device of claim 22, wherein:
the actuator moves proximally with respect to the barrel to move the first and second self-supporting snare loops in unison to the retracted configuration; and
the actuator moves distally with respect to the barrel to move the first and second self-supporting snare loops in unison to the radially extended configuration.

25. The device of claim 22,
wherein the first self-supporting snare loop and the second self-supporting snare loop exit radially outward and in opposite directions from the distal tip without the distal tip axially shortening with respect to the barrel when changing between the retracted configuration and the radially extended configuration.

26. The device of claim 22, wherein the first self-supporting snare loop and the second self-supporting snare loop are detached and separate from any sharp needles.

27. The device of claim 22, wherein retraction of the first self-supporting snare loop and the second self-supporting snare loop in unison closes the first opening and the second opening while simultaneously capturing the first suture portion and the second suture portion.

\* \* \* \* \*